United States Patent [19]

Parkinson et al.

[11] Patent Number: 5,175,327

[45] Date of Patent: Dec. 29, 1992

[54] PROCESS FOR THE PREPARATION OF SILONAL ALKOXYLATES

[75] Inventors: Jeff K. Parkinson, Lawrenceville; Anthony J. O'Lenick, Jr., Lilburn, both of Ga.

[73] Assignee: Siltech Inc., Norcross, Ga.

[21] Appl. No.: 826,040

[22] Filed: Jan. 27, 1992

[51] Int. Cl.⁵ ............................ C07F 7/08; C07F 7/18
[52] U.S. Cl. .................................................. 556/446
[58] Field of Search ........................................ 556/446

[56] References Cited

U.S. PATENT DOCUMENTS

| | | | |
|---|---|---|---|
| 2,834,748 | 5/1958 | Bailey et al. | 556/446 X |
| 3,272,762 | 9/1966 | Ibbotson et al. | 556/446 X |
| 3,480,583 | 11/1969 | Bailey et al. | 556/446 |
| 3,541,127 | 11/1970 | Beattie et al. | 556/446 |
| 3,836,560 | 9/1974 | Prokai et al. | 556/446 |
| 3,980,688 | 9/1976 | Litteral et al. | 556/446 |
| 4,490,416 | 12/1984 | Westall et al. | 556/446 X |
| 4,578,116 | 3/1986 | Rott et al. | 556/446 X |
| 4,616,076 | 10/1986 | Ona et al. | 556/446 X |
| 4,886,551 | 12/1989 | Fink et al. | 556/446 X |

*Primary Examiner*—Paul F. Shaver

[57] ABSTRACT

The invention discloses novel silanol ether compounds. Compounds of the invention are prepared by the ethoxylation and/or propoxylation of the hydroxyl group in the silanol compound. By virtue of their silanol backbone these compounds are highly lubricious and provide outstanding lubrication and hydrophobicity when applied to hair, skin and textile fibers. The incorporation of alkylene oxide into the backbone results in a self emulsifying product which is surprisingly effective in delivering silicone to the substrate being treated. The compounds of the present invention are prepared by reacting a silanol compound with ethylene oxide and/or propylene oxide in the presence of a suitable catalyst.

13 Claims, No Drawings

PROCESS FOR THE PREPARATION OF SILONAL ALKOXYLATES

BACKGROUND OF THE INVENTION

1. Field of the Invention

The compounds of the present invention are novel silanol ether compounds. Compounds of the invention are prepared by the ethoxylation and/or propoxylation of the hydroxyl group in the silanol compound. By virtue of their silanol backbone these compounds are highly lubricious and provide outstanding lubrication and hydrophobicity when applied to hair, skin and textile fibers. The incorporation of alkylene oxide into the backbone results in a self emulsifying product which is surprisingly effective in delivering silicone to the substrate being treated. The compounds of the present invention are prepared by reacting a silanol compound with ethylene oxide and/or propylene oxide in the presence of a suitable catalyst.

The present invention relates to a series of novel silanol alkoxylates which provide outstanding lubrication, and hydrophobicity to a variety of substrates and are self emulsifying. This aspect of the invention makes it possible for the compounds to be applied from aqueous dispersion without the addition of surfactants which minimize the effectiveness of the application to the substrate being treated.

2. Arts and Practices

Silicone compounds have been known to be active at the surface of plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quats are the active ingredient in traditional laundry care markets, with little or no silicone added.

The low efficiency and low durability of polydimethylsiloxane is due to the fact that it is very water insoluble and deposits on the surface to obtain a minimum free energy in the solution. Simply, the silicone oil delivery to the surface by hydrophobic binding, not chemical bonding. At the surface, the polydimethylsiloxane is a very effective fiber lubricant, however, there are two drawbacks, first; the polydimethylsiloxane is not chemically bonded so the effect is very transient and disappears with one washing, and second; since there is no reaction of the siloxane to the surface an equilibrium between fiber absorbed polydimethylsiloxane and polydimethylsiloxane in the dispersion results in very inefficient percentage of silicone deposited. A large amount of the expensive silicone goes down the drain with the waste water.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds the efficiency and durability of the were not good enough to allow for cost effective incorporation of these materials in detergent formulations.

THE INVENTION

Object of the Invention

It is the object of the present invention to provide novel alkoxylated silanol compounds which can be prepared having different solubilities in many solvents. This is attained by proper selection of the type and location of the alkylene oxide used.

It is another objective of the current invention to provide alkoxylated silanol compounds which can be used in textile, and personal care applications to render softness and lubrication to the substrates being treated. The self emulsifying properties, the superior antistatic properties are each important benefits. Application of the compounds of the invention can be from solvent, aqueous dispersion or solution, or applied neat in these processes.

SUMMARY OF THE INVENTION

The present invention relates to alkoxylated silanol compounds. The compounds by virtue of the silanol ether group form effective surface self emulsifying modifying finishes. The compounds of the present invention are substantive to cellulosic and synthetic fibers as well as metal surfaces and plastic polymers.

The compounds of this invention are silanol ethers made by the alkoxylation of a silanol compound with ethylene oxide, propylene oxide or mixtures thereof. The compounds of the present invention conform to the following structure:

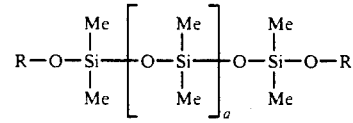

wherein
Me is methyl;
R is $-(CH_2-CH_2-O)_b-(CH_2-CH(CH_3)O)_c-(CH_2-CH_2-O)_d-H$;
b, c, and d each independently range from 0 to 200, with the proviso that $b+c+d$ be greater than 0;
a is an integer from 1 to 2,000.

We have surprisingly learned that the silanol hydroxyl group of the silicone molecule alkoxylates to give novel surface active ether compounds. Prior to this invention it was assumed that the addition of alkaline of acid catalysts useful for alkoxylation would cause polymerization of the silanol and not the desired reaction with the alkyene oxide.

It must be clearly understood that the silanol hydroxyl is appreciably different from the hydroxyl group which is located on a carbon atom (i.e. an alcohol). The hydroxyl group on the alcohol is stable to polymerization. The alkoxylation product produced using the alcohol is very hydrolytically stable, while the silanol ether has more limited stability over a range of pH values. The silanol ether behaves more like the carbon based ester in terms of hydrolytic stability over a pH range than it does like the carbon based alcohol alkoxylate.

Additionally, the raw material silanol compound can undergo homopolymerization with the splitting off of water to form a new Si—O—Si bond. This was the anticipated product under alkoxylation conditions. To our surprise, this reaction did not occur, rather alkoxylation occurred in very high yield.

Desired Silanol Reaction Sequence

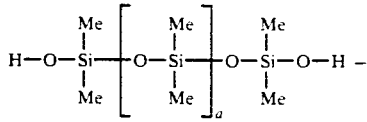

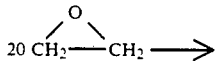

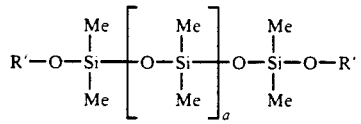

R' is $-(CH_2-CH_2-O)10-H$.

We soon learned that the alkoxylates so produced have surface active properties. They can be made to differing solubilities in water, or other solvents by varying the amount and location of the oxide residue in the backbone.

We also learned that the location and amount of propylene oxide in the backbone has a profound effect upon the hydrolytic stability of the resultant ether. In a preferred embodiment, the propylene oxide is placed directly onto the silanol hydroxyl group. (i.e. b is zero, c is a value between one and five and d is greater than zero).

In another preferred embodiment, b is zero, c is a value between one and four and d is greater than five. This gives the desired dispersibility in water.

In still another preferred embodiment, b is zero, c is a value between one and four and d is greater than ten. This gives the product solubility in water.

In a preferred embodiment, a is between 20 and 2,000. This gives the product partial solubility in silicone oil.

In another preferred embodiment, a is between 500 and 1,000. This gives the product optimum solubility/dispersibility in both water and silicone oil.

The compounds of the present invention are very effective self dispersing conditioning agents for fiber. The compounds are contacted with the fiber in an effective conditioning amount. In a preferred embodiment, the effective conditioning amount ranges from 0.01% to 30% by weight.

In another preferred embodiment, the effective conditioning amount ranges from 0.1% to 20% by weight. In still another preferred embodiment the effective conditioning amount ranges from 1% to 10% by weight.

EXAMPLES

The compounds of the present invention are prepared by the reaction of a silanol compound with ethylene oxide and or propylene oxide.

Silanol Compounds

Silanol compounds are well known and are marketed in the trade under many names. The compounds conform to the following generic structure;

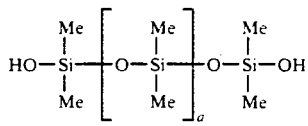

Me is methyl and a ranges from 1 to 2,000.

Compounds conforming to the above structure are available from Siltech Inc. Norcross, Ga. and are marketed under the Siltech S series tradename shown;

| Name | Molecular Weight | Value of "a" |
| --- | --- | --- |
| Siltech S 700 | 500 | 4 |
| Siltech S 701 | 1,000 | 11 |
| Siltech S 706 | 6,000 | 79 |
| Siltech S 710 | 10,000 | 133 |
| Siltech S 750 | 50,000 | 673 |
| Siltech S 790 | 86,000 | 1160 |
| Siltech S HV | 150,000 | 2000 |

General Reaction Conditions

The alkoxylation vessel useful for the preparation of the compounds are well known to those skilled in the art and are available for example from Parr Inc.

The exact conditions used for alkoxylation can be varied over a relatively wide range. These conditions are typical;

1. To a clean, dry alkoxylation vessel having the ability to heat the contents to 200° C. and having the ability to accommodate pressures of up th 100 psi, add the silanol/
2. Add the specified amount of the specified catalyst under good agitation.
3. If ethylene oxide is to be added first, add the ethylene oxide, at between 260-290 F. and 45 psig.
4. After all the ethylene oxide has been added, hold for one hour. Apply vacuum strip to remove any residual low levels of ethylene oxide.
5. If propylene oxide is being added propoxylate at 290-300 F. and 45 psig.
6. After all the propylene oxide has been added, hold for one hour. Apply vacuum strip to remove any residual low levels of propylene oxide.
7. If ethylene oxide is to be added again, add all the ethylene oxide, at between 260-290 F. and 45 psig.
8. After all the ethylene oxide has been added, hold for one hour. Apply vacuum strip to remove any residual low levels of ethylene oxide.

The process can be alternated using any amount of ethylene oxide, propylene oxide or mixtures thereof.

EXAMPLE 1

The product is prepared according to the following procedure;

1. To a clean, dry alkoxylation vessel having the ability to heat the contents to 200° C. and having the ability to accommodate pressures of up th 100 psi, add 500.0 grams of Siltech S 700 (the silanol).
2. Add the 0.1% by weight (based upon the total weight of product to be produced) KOH powder under good agitation. (In this case 0.1% of 3,440.0 grams or 34.4 grams)
3. Add 880 grams of ethylene oxide at between 260-290 F. and 45 psig.

4. After all the ethylene oxide has been added, hold for one hour. Apply vacuum strip to remove any residual low levels of ethylene oxide.

5. Add 1180.0 grams of propylene oxide at 290–300 F. and 45 psig.

6. After all the propylene oxide has been added, hold for one hour. Apply vacuum strip to remove any residual low levels of propylene oxide.

7. Add the last 880 grams of ethylene oxide at between 260–290 F. and 45 psig.

8. After all the ethylene oxide has been added, hold for one hour. Apply vacuum strip to remove any residual low levels of ethylene oxide.

The product is used without additional purification.

EXAMPLE 2-37

Example 1 is repeated, only this time the specified amount of the specified silanol is used in place of S 700. The specified amount and type of catalyst is used in place of the specified amount of KOH and the specified amounts of oxide are used in place of the amounts of ethylene oxide (EO 1), propylene oxide (PO) and ethylene oxide (EO 2) specified.

| Catalysts Types | | |
|---|---|---|
| A | Sodium Methoxide (NaOCH$_3$) | 0.2% of total batch weight |
| B | Sodium Methoxide (NaOCH$_3$) | 0.1% of total batch weight |
| C | Sodium Hydroxide (NaOH) | 0.2% of total batch weight |
| D | Sodium Hydroxide (NaOH) | 0.1% of total batch weight |
| E | Phosphoric Acid (H$_3$PO$_4$) | 0.2% of total batch weight |

| Example Number | Silanol Type/grams | Catalyst System | EO 1 grams | PO grams | EO 2 grams |
|---|---|---|---|---|---|
| 1 | S 700/500 | A | 880 | 1180 | 880 |
| 2 | S 701/1,000 | A | 0 | 44 | 0 |
| 3 | S 706/6,000 | A | 0 | 59 | 220 |
| 4 | S 710/10,000 | A | 0 | 120 | 880 |
| 5 | S 750/50,000 | A | 0 | 180 | 400 |
| 6 | S 790/86,000 | A | 0 | 236 | 220 |
| 7 | S HV/150,000 | A | 0 | 1180 | 880 |
| 8 | S 700/500 | A | 0 | 500 | 500 |
| 9 | S 701/1,000 | A | 0 | 50 | 50 |
| 10 | S 706/6,000 | A | 880 | 1180 | 880 |
| 11 | S 710/10,000 | A | 100 | 0 | 0 |
| 12 | S 750/50,000 | A | 25 | 0 | 0 |
| 13 | S 790/86,000 | A | 880 | 0 | 0 |
| 14 | S HV/150,000 | A | 500 | 0 | 0 |
| 15 | S 700/500 | B | 5 | 0 | 0 |
| 16 | S 701/1,000 | B | 0 | 100 | 20 |
| 17 | S 706/6,000 | B | 500 | 500 | 500 |
| 18 | S 710/10,000 | B | 880 | 1180 | 200 |
| 19 | S 750/50,000 | B | 120 | 10 | 200 |
| 20 | S 790/86,000 | B | 10 | 1 | 10 |
| 21 | S HV/150,000 | B | 50 | 1000 | 50 |
| 22 | S 700/500 | B | 500 | 10 | 800 |
| 23 | S 701/1,000 | B | 200 | 10 | 190 |
| 24 | S 706/6,000 | B | 100 | 45 | 0 |
| 25 | S 710/10,000 | B | 150 | 3 | 0 |
| 26 | S 750/50,000 | B | 25 | 45 | 45 |
| 27 | S 790/86,000 | B | 35 | 1180 | 56 |
| 28 | S HV/150,000 | B | 23 | 0 | 0 |
| 29 | S 700/500 | C | 16 | 3 | 3 |
| 30 | S 701/1,000 | C | 12 | 54 | 0 |
| 31 | S 706/6,000 | C | 54 | 500 | 500 |
| 32 | S 710/10,000 | C | 44 | 10 | 10 |
| 33 | S 750/50,000 | C | 59 | 5 | 5 |
| 34 | S 790/86,000 | C | 800 | 0 | 0 |
| 35 | S HV/150,000 | C | 450 | 300 | 300 |
| 36 | S 700/500 | D | 650 | 650 | 650 |
| 37 | S 701/1,000 | D | 98 | 1 | 10 |

EO 1 refers to the first addition of ethylene oxide.
PO refers to the addition of propylene oxide.
EO 2 refers to the second addition of ethylene oxide.
Therefore in the generic structure where R is
—(CH$_2$—CH$_2$—O)$_b$—(CH$_2$—CH(CH$_3$)O)$_c$—(CH$_2$—CH$_2$—O)$_d$—H:

|←— EO 1 —→|←— PO —→|←— EO 2 —|

APPLICATION EXAMPLES

Lubrication
FRICTIONAL PROPERTIES

| PRODUCT | DESCRIPTION (70 F) | LUBRICATION DATA[1] Coefficient of Friction FIBER/METAL | |
|---|---|---|---|
| | | 100 | 300 |
| | | (m/min.) | |
| Butyl Stearate | White Liquid | 0.17 | 0.21 |
| Tridecyl Stearate | Clear Liquid | 0.25 | 0.27 |
| Example 17 | Clear Liquid | 0.10 | 0.11 |
| Example 25 | Clear Liquid | 0.07 | 0.09 |
| Example 32 | Clear Liquid | 0.06 | 0.02 |
| Example 12 | Clear Liquid | 0.09 | 0.04 |
| Ditallowdimethyl benzalkonium chloride | Tan solid | 0.35 | 0.35 |
| Ditridecyl adipate | Clear Amber Liquid | 0.28 | 0.29 |
| Siltech CE-2000 (tri-Octyl-dodecyl citrate) | Clear Liquid | 0.20 | 0.20 |
| Untreated Fiber | | 0.98 | 1.01 |

[1]Rothchild F Meter. Fiber: 150 denier polyester. Temperature: 72 F., Relative humidity: 60%

As can be easily seen the compounds of the present invention are excellent lubricants.

What is claimed:

1. A process for the preparation of a silicone polymer which comprises the alkoxylation reaction of a silanol compound conforming to the following structure;

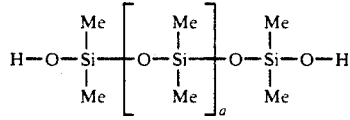

wherein
Me is methyl;
a is an integer from 4 to 2,000;
with an alkylene oxide selected from the group consisting of ethylene oxide, propylene oxide and mixtures thereof in the presence of a catalyst selected from the group consisting of potassium hydroxide, sodium methoxide, sodium hydroxide and phosphoric acid.

2. A process of claim 1 wherein; b is zero; c is a integer ranging from one to five and d is greater than zero.

3. A process of claim 1 wherein b is zero, c is an integer ranging from one to four and d is greater than five.

4. A process of claim 1 wherein b is zero; c is an integer ranging from one to four and d is greater than ten.

5. A process of claim 1 wherein a is an integer ranging from 15 to 2,000.

6. A process of claim 1 wherein a is an integer ranging from 20 to 1,000.

7. A process of claim 1 wherein a is an integer ranging from 5000 to 1,000.

8. A process of claim 1 wherein in said reaction is conducted using ethylene oxide at a temperature of between 260-290 F.

9. A process of claim 1 wherein said reaction is conducted using propylene oxide at a temperature of between 290-300 F.

10. A process of claim 1 wherein said catalyst is potassium hydroxide.

11. A process of claim 1 wherein said catalyst is sodium methoxide.

12. A process of claim 1 wherein said catalyst is sodium hydroxide.

13. A process of claim 1 wherein said catalyst is phosphoric acid.

* * * * *